(12) United States Patent
Hosogai et al.

(10) Patent No.: US 11,776,902 B2
(45) Date of Patent: Oct. 3, 2023

(54) SEMICONDUCTOR DEVICE, AN IMAGE UNIT AND AN ENDOSCOPE SYSTEM

(71) Applicant: OLYMPUS CORPORATION, Tokyo (JP)

(72) Inventors: Katsumi Hosogai, Tshukuba (JP); Satoru Adachi, Tsuchiura (JP); Takatoshi Igarashi, Tokyo (JP); Satoshi Nasuno, Tokyo (JP)

(73) Assignee: Olympus Corporation, Tokyo (JP)

( * ) Notice: Subject to any disclaimer, the term of this patent is extended or adjusted under 35 U.S.C. 154(b) by 112 days.

(21) Appl. No.: 17/375,314

(22) Filed: Jul. 14, 2021

(65) Prior Publication Data

US 2022/0028782 A1      Jan. 27, 2022

Related U.S. Application Data

(60) Provisional application No. 63/054,869, filed on Jul. 22, 2020.

(51) Int. Cl.
*H01L 23/522* (2006.01)
*H01L 27/146* (2006.01)
*A61B 1/05* (2006.01)

(52) U.S. Cl.
CPC ............ *H01L 23/5226* (2013.01); *A61B 1/05* (2013.01); *H01L 23/5223* (2013.01); *H01L 27/14603* (2013.01)

(58) Field of Classification Search
CPC ............ H01L 23/5226; H01L 23/5223; H01L 27/14603; A61B 1/05
USPC .......................................................... 257/532
See application file for complete search history.

(56) References Cited

U.S. PATENT DOCUMENTS

2017/0250159 A1*   8/2017   Lee ...................... H01L 23/481

* cited by examiner

*Primary Examiner* — Tu-Tu V Ho
(74) *Attorney, Agent, or Firm* — Morgan, Lewis & Bockius LLP

(57) ABSTRACT

A semiconductor device includes a semiconductor substrate, a trench capacitor arranged on the semiconductor substrate, a first wiring layer, a second wiring layer, a first TSV penetrating the semiconductor substrate outside the trench capacitor, a second TSV penetrating the semiconductor substrate outside the trench capacitor, a first connecting terminal connected to the first TSV, a second connecting terminal connected to the first TSV, a third connecting terminal connected to the second TSV, and a fourth connecting terminal connected to the second TSV. A plurality of connecting terminals including the first through fourth connecting terminals are arranged dispersively over an entire area of the first wiring layer and the second wiring layer of the semiconductor device, thereby stabilizing voltage supplied to an image unit and achieving a stable image signal.

17 Claims, 10 Drawing Sheets

SEMICONDUCTOR DEVICE, AN IMAGE UNIT AND AN ENDOSCOPE SYSTEM

RELATED APPLICATION DATA

This application is based on and claims priority under 35 U.S.C. § 119 to U.S. Provisional Application No. 63/054,869, filed Jul. 22, 2020, the entire contents of which are incorporated herein by reference.

FIELD OF THE INVENTION

The present invention relates to a semiconductor device, an image unit and an endoscope system using the semiconductor device, and more particularly, to a semiconductor device having a trench capacitor, an image unit and an endoscope system using the semiconductor.

DESCRIPTION OF RELATED ART

A semiconductor device having a trench capacitor typically includes the trench capacitor in a substrate of the semiconductor. The semiconductor device uses the trench capacitor to accumulate electric charge for stabilizing a value of VDD voltage supplied to an electrical circuit of an image unit such as an image sensor or the like. The semiconductor device may have a plurality of trenches formed on its surface and have a plurality of electrodes buried in the plurality of trenches, respectively, thereby forming trench capacitors. By supplying the VDD voltage and GND voltage to the electrodes, the trench capacitors accumulates electric charge.

An endoscope system using the semiconductor device typically includes an endoscope and a processor unit. The processor unit controls a voltage source to supply VDD voltage (power supply voltage) and GND voltage (ground voltage) to the endoscope. The endoscope includes an image sensor provided at a distal end portion of the endoscope. The image senor is used to generate an image signal by using the VDD voltage and GND voltage supplied from the voltage source. The VDD voltage supplied to the image sensor has a fixed value (such as 3.3V) at normal operation. However, the value of VDD voltage can drop by the disturbance or the like. In this situation, the image sensor cannot generate a stable image signal. Therefore, there is a need to provide a semiconductor device that is capable of stabilizing the VDD voltage supplied to the image sensor.

The image sensor and the semiconductor device having the trench capacitors are usually stacked for stabilizing VDD voltage supplied to the image sensor. In this case, TSVs (Through Silicon Via) are arranged at the semiconductor device for supplying VDD voltage and GND voltage to the semiconductor device and the image sensor respectively.

In the related art, a plurality of semiconductor substrates utilizing the TSVs are stacked together. For example, when a plurality of DRAM (Dynamic Random Access Memory) substrates are stacked, the TSVs are typically arranged at the edge regions of these DRAM substrates. The edge region is an outer region of the DRAM on the surface of the semiconductor substrate. The plurality of semiconductor substrates are stacked and connected at the TSVs position with each other. The GND voltage and VDD voltage are supplied to each DRAM substrate by using the TSVs. Each semiconductor substrate has the TSVs for transmitting the GND voltage, VDD voltage and signals. However, in the case that the semiconductor substrate having the TSVs at the edge region is connected at the TSV position, there is a problem that the semiconductor substrate is subject to be damaged by stress concentration at the TSV position by a bump connection process or the like. This problem easily occurs particularly when the small and thin semiconductor substrates are stacked and connected each other.

SUMMARY OF THE INVENTION

Accordingly, the present invention is directed to a semiconductor device having a trench capacitor, an image unit and an endoscope system that substantially obviates one or more of the problems due to limitations and disadvantages of the related art.

An object of the present invention is to provide a semiconductor substrate having a first surface and a second surface opposing to each other, a trench capacitor arranged on the first surface of the semiconductor substrate, a first wiring layer arranged on the first surface of the semiconductor substrate and covering the trench capacitor, a second wiring layer arranged on the second surface of the semiconductor substrate, a first TSV (through-silicon via) penetrating the semiconductor substrate at an outer area of the trench capacitor, a second TSV (through-silicon via) penetrating the semiconductor substrate at the outer area of the trench capacitor, a first connecting terminal arranged on the first wiring layer, and connected to the first TSV, a second connecting terminal arranged on the second wiring layer, and connected to the first TSV, a third connecting terminal arranged on the first wiring layer, and connected to the second TSV, and a fourth connecting terminal arranged on the second wiring layer, and connected to the second TSV, wherein a plurality of connecting terminals including the first through fourth connecting terminals are arranged dispersively over an entire area of the first wiring layer and the second wiring layer of the semiconductor device.

Another object of the present invention is to provide an image unit including an image sensor and a semiconductor device. The image sensor includes an image pixel formed on a first surface, and a ground terminal and a VDD terminal on a second surface. The semiconductor device includes the first and third connecting terminals that are connected with the VDD and the ground terminals of the image sensor, respectively.

Still another object of the present invention is to provide an endoscope system that utilize the image unit and the semiconductor device. Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE PREFERRED EMBODIMENT

Figure 1:
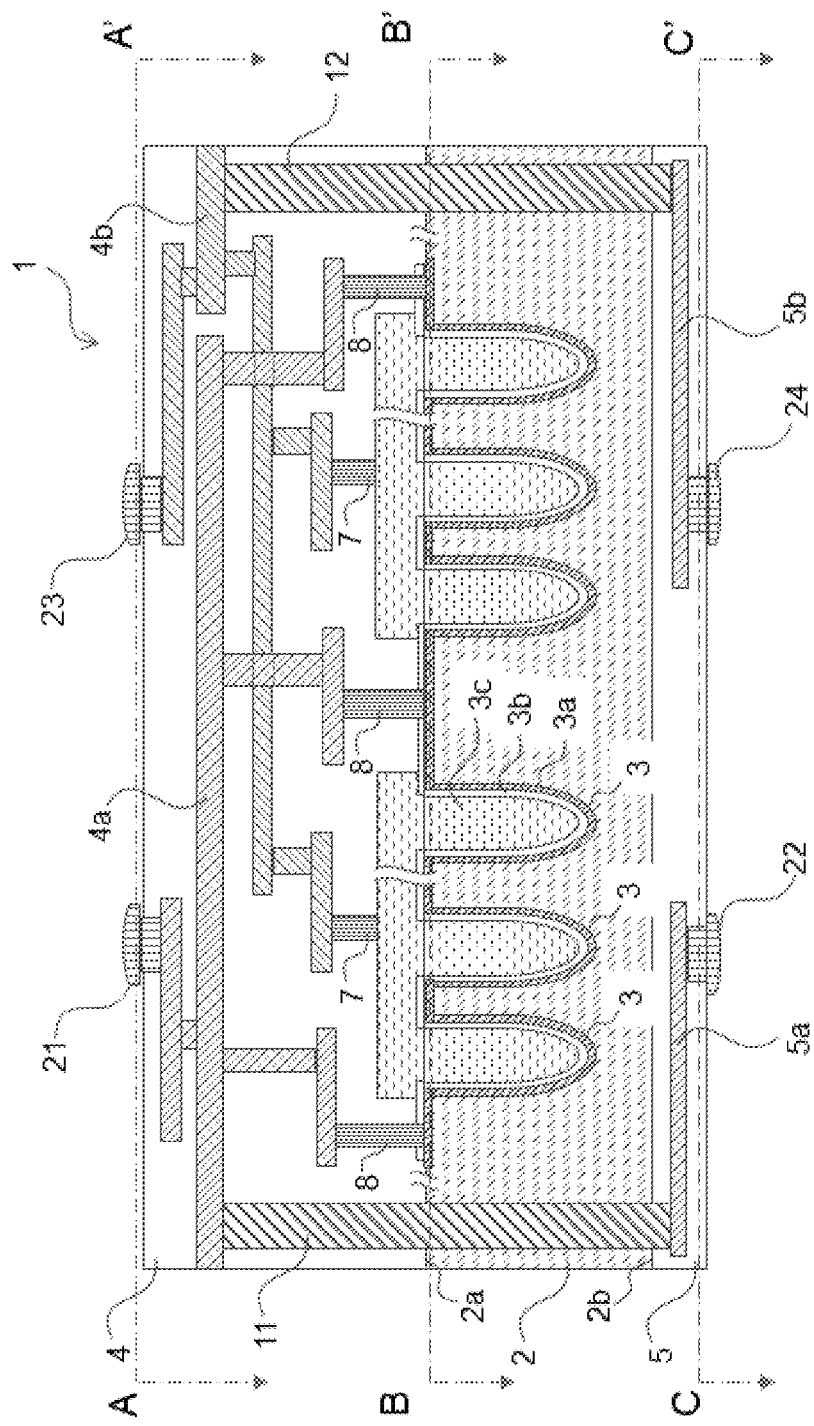
FIG. 1 is a cross section view schematically illustrating a semiconductor device according to a first exemplary embodiment.
Figure 2:
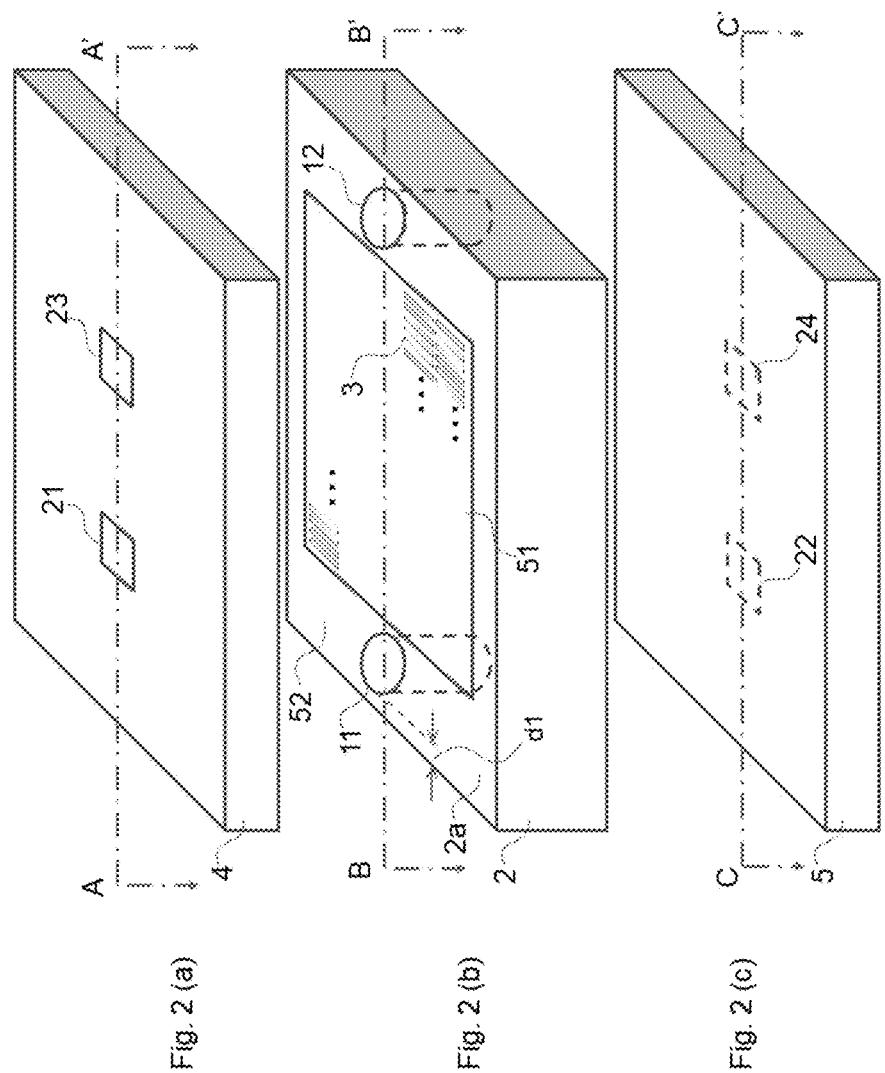
FIGS. 2(a) to (c) are perspective views schematically illustrating certain components of the semiconductor device of FIG. 1.

Reference will now be made in detail to the preferred embodiments of the present invention, examples of which are illustrated in the accompanying drawings. FIG. 1 is a cross section view schematically illustrating a semiconductor device according to a first exemplary embodiment. FIGS. 2(a) to 2(c) are perspective views schematically illustrating certain components of the semiconductor device of FIG. 1. FIGS. 3(a) to 3(c) are plain views schematically illustrating the components of FIG. 2, respectively.

FIG. 3(a) indicates a plain view with respect to the arrows A-A' of FIG. 1 and FIG. 2 (a). FIG. 3(b) indicates a plain view with respect to the arrows B-B' of FIG. 1 and FIG. 2 (b). FIG. 3(c) indicates a plain view with respect to the arrows C-C' of FIG. 1 and FIG. 2 (c).

As shown in FIG. 1, a semiconductor device 1 may include a semiconductor substrate 2, a trench capacitor 3 embedded in the semiconductor substrate 2, a first wiring layer 4 covering a front surface of the semiconductor substrate 2, a second wiring layer 5 covering a rear surface of the semiconductor substrate 2. The semiconductor device 1 may also include a first TSV (Through Silicon Via) 11 and a second TSV 12 that penetrate the semiconductor substrate 2 at an outer area of the trench capacitor 3, which is outside the trench capacitor area. The semiconductor device 1 may further include a plurality of connecting terminals. As shown in FIG. 1 for example, the plurality of connecting terminals may include at least a first connecting terminal 21, a second connecting terminal 22, a third connecting terminal 23, and a fourth connecting terminal 24, which may be arranged dispersively on the front and rear surfaces of the semiconductor substrate 2. For example, the first and second connecting terminals 21 and 22 may be arranged on the front surface of the semiconductor substrate 2, and the third and fourth connecting terminals 23 and 24 may be arranged on the rear surface of the semiconductor substrate 2. Moreover, the first and second connecting terminals 21 and 22 may be evenly arranged on the front surface of the semiconductor substrate 2 along with additional connecting terminals in a regular interval with one another. The third and fourth connecting terminals 23 and 24 may be evenly arranged with different additional connecting terminals on the rear surface of the semiconductor substrate 2 in a regular interval with one another.

The semiconductor substrate 2 may be a square or rectangle plate shape, or may be formed in a shape that is suitable for an electronic device that utilizes the semiconductor substrate 2. The semiconductor substrate 2 may have a horizontal width and a vertical width, each of which widths may be in a range of 500 micrometer to 1500 micrometer. The thickness of the semiconductor substrate 2 may be in a range of 40 micrometer to 60 micrometer.

The semiconductor substrate 2 includes a first surface 2a and a second surface 2b facing each other. As shown in FIG. 1, the first surface 2a may be the front surface of the semiconductor substrate 2, and the second surface 2b may be the rear surface of the semiconductor substrate 2. Also, a plurality of trench capacitors 3 may be arranged on the first surface 2a. In this embodiment, the trench capacitors 3 may be spaced apart from each other in a regular interval with one another, and evenly substantially occupy the entire area of the first surface 2a except for a periphery region of the first surface 2a. Each of the trench capacitors 3 may include a first electrode 3a, a dielectric layer 3b, and a second electrode (buried electrode) 3c.

The trench capacitors 3 may be formed as follows. A plurality of trenches may be formed on the first surface 2a by a dry etching process or the like. A membranous metal layer may be formed as a first electrode 3a for each trench capacitor 3 by a vapor deposition process or the like. The first electrode 3a covers the plurality of trenches. Then, a membranous dielectric layer 3b may be formed on and cover the first electrode 3a. After that, a second electrode 3c is partially buried into the trenches that are covered by the first electrode 3a and the dielectric layer 3b, such that the first electrode 3a and the second electrode 3c sandwich the dielectric layer 3b. For example, the depth of the trench capacitor 3 may be in a range of 5 micrometer to 20 micrometer. The pitch of each trench capacitor 3, or a distance between the trench capacitors 3, may be in a range of 1 micrometer to 3 micrometer.

The plurality of trench capacitors 3 may be divided into a plurality of groups of trench capacitors 3 when arranging these trench capacitors 3. For example, each group of trench capacitors 3 may include at least three (3) to ten (10) trench capacitors 3. In this embodiment, the left side of FIG. 1 shows a first group of trench capacitors 3 (only three trench capacitors 3 are shown at the left side in a cross-sectional view). The first group of trench capacitors 3 may share one second electrode 3c. The right side of FIG. 1 shows a second group of trench capacitors 3 (only three trench capacitors 3 are shown at the right side in a cross-sectional view). The second group of trench capacitors 3 may share a different second electrode 3c. The first electrode 3a and dielectric layer 3b are also shared in the same or similar manner as the second electrode 3c. The first wiring layer 4 may include a plurality of gate contacts 7 and a plurality of substrate contacts 8. The gate contacts 7 and the substrate contacts 8 are connected to the plurality trench capacitor 3. As shown in FIG. 1, the gate contact 7 may be connected to the second electrode 3c by contacting a part of the second electrode 3c that is exposed outside of the trench capacitor 3. The first electrode 3a includes a first portion that is formed inside the trenches, and a second portion that is disposed outside the trenches on the first surface 2a. The substrate contact 8 may be connected to the first electrode 3a by directly contacting the second portion of the first electrode 3a that is disposed outside the trenches. As described later, a VDD voltage may be supplied to the substrate contact 8, and a GND voltage may be supplied to the gate contact 7.

FIGS. 2(*a*) to 2(*c*) are perspective views schematically illustrating certain components of the semiconductor device 1 of FIG. 1. As shown in FIG. 2(*b*), the plurality of trench capacitor 3 are formed in parallel with each other. The length of the longitudinal direction of each trench capacitor 3 may be in a range of 5 micrometer to 10 micrometer. The reference numeral 51 denotes a trench capacitor area where the trench capacitors 3 are formed on the first surface 2*a* of the semiconductor substrate 2. The trench capacitor area 51 occupies a first part of the first surface 2*a*. The first part 51 of the first surface 2*a* may have a size up to 80% of the entire area of the first surface 2*a* so as to increase the amount of electric charge. A second part 52 in FIG. 2(*b*) of the first surface 2*a* surrounds the first part 51 to provide an area that may be used by the first TSV (Through Silicon Via) 11, the second TSV 12, and other elements necessary for the semiconductor device 1.

Referring back to FIG. 1, the first wiring layer 4 is formed on the first surface 2*a* of the semiconductor substrate 2. The first wiring layer 4 covers the trench capacitor 3. The second wiring layer 5 is formed on the second surface 2*b* of the semiconductor substrate 2. The first wiring layer 4 includes an insulator layer in which a plurality of wirings such as wirings 4*a* and 4*b* are embedded. The second wiring layer 5 includes an insulator layer in which a plurality of wirings such as wirings 5*a* and 5*b* are embedded.

The first TSV 11 and the second TSV 12 penetrate the semiconductor substrate 2 in a thickness direction between the first surface 2*a* and the second surface 2*b*. As shown in FIG. 2(*b*) and FIG. 3 (*b*), the first TSV 11 and the second TSV 12 are arranged at an area outside the trench capacitor area 51, which is referred to as an outer area of the trench capacitor area 51 and corresponds to the second part of the first surface 2*a* of the semiconductor substrate 2.

The first TSV 11 and the second TSV 12 may be configured at the semiconductor substrate 2 as follows. A plurality of TSV holes may be formed at the semiconductor substrate 2 in the thickness direction by a dry etching process or the like. After that, a conductor material such as Cu metal may be buried in the TSV holes by a plating process or the like. For example, a diameter of the first TSV 11 may be in a range of 10 to 50 micrometer. A distance d1 from the edge of the semiconductor substrate 2 to the outer end of the first TSV 11 may be set in a range of 10 to 20 micrometer.

As shown in FIG. 1, the first connecting terminal 21 and the third connecting terminal 23 may be arranged on an outer surface (exposed surface) of the first wiring layer 4. The second connecting terminal 22 and the fourth connecting terminal 24 may be arranged on an outer surface (exposed surface) of the second wiring layer 5.

The first TSV 11 may be connected to the first connecting terminal 21 by the wiring 4*a* of the first wiring layer 4. The second TSV 12 may be connected to the third connecting terminal 23 by the wiring 4*b* of the first wiring layer 4. The first TSV 11 may be connected to the second connecting terminal 22 by the wiring 5*a* of the second wiring layer 5. The second TSV 12 may be connected to the fourth connecting terminal 24 by the wiring 5*b* of the second wiring layer 5.

Figure 3:
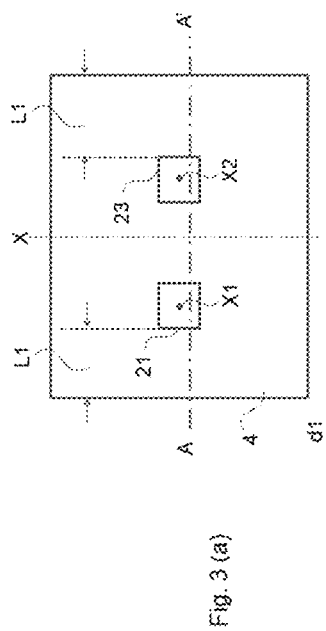
FIGS. 3(a) to 3(c) are plain views schematically illustrating the components of FIGS. 2(a) to 2(c), respectively.
Figure 3:
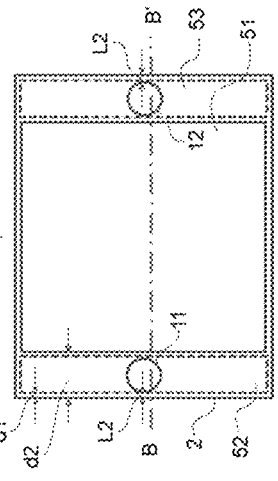
Figure 3:
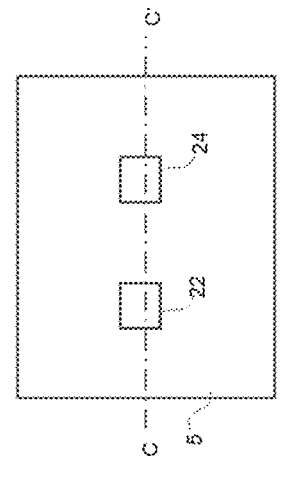

Next, a description of arranging the TSVs and the connecting terminals is given as follows. As shown in FIG. 3(*b*), the first TSV 11 and the second TSV 12 may be arranged at the outer area of the trench capacitor area 51. The outer area of the trench capacitor area 51 includes surrounding areas 52, 53 that surrounds the trench capacitor area 51 occupied by the trench capacitors 3 on the first surface 2*a*. In other words, the trench capacitor area 51 may substantially occupy the entire area of the first surface 2*a* of the semiconductor substrate 2 except for the surrounding areas 52 and 53.

As shown in FIG. 3 (*b*), in this exemplary embodiment, the surrounding areas 52 and 53 may be left and right edge regions of the semiconductor substrate 2. In particular, the surrounding area 52 may be the left region from the left edge of the semiconductor substrate 2 to the outer end of the trench capacitor area 51. The surrounding area 53 may be the right region from the right edge of the semiconductor substrate 2 to the outer end of the trench capacitor area 51. For example, a distance d2 from the edge of the semiconductor substrate 2 to the outer end of the trench capacitor area 51 may be set in a range of 20 to 70 micrometer.

On the other hand, the plurality of connecting terminals including the first, second, third and fourth connecting terminals 21, 22, 23 and 24 may be dispersively arranged over the entire area of the first wiring layer 4 and the second wiring layer 5 of the semiconductor device 1. For example, the plurality of connecting terminals may be arranged evenly and spaced apart from one another in a predetermined interval. These connecting terminals may also be arranged in one pattern on the first wiring layer 4, and in a different pattern on the second wiring layer 5. These connecting terminals may also be arrange in different patterns on any one of the first wiring layer 4 and the second wiring layer 5. The arrangement of these connecting terminals should be made to effectively utilize the entire area of the first wiring layer 4 and the second wiring layer 5 of the semiconductor device 1 without overlapping with other elements that are arranged at an edge area of the semiconductor substrate 2. For example, as shown in FIGS. 2(*a*)-2(*c*), the plurality of the connecting terminals 21, 22, 23 and 24 do not overlap with the TSVs 11 and 12 from a top view of the semiconductor device 1.

As shown in FIG. 3 (*a*), the first connecting terminal 21 and the third connecting terminal 23 are "arranged dispersively" on the first wiring layer 4 with respect to the entire area of the first wiring layer 4. An exemplary manner of arranging the first connecting terminal 21 and the third connecting terminal 23 on the first wiring layer 4 in a dispersive manner (the meaning of "arranged dispersively") is described as follows.

The first connecting terminal 21 and third connecting terminal 23 may be evenly spaced apart on the first wiring layer 4 with respect to the entire area of the first wiring layer 4. The region where the first and third connecting terminals 21 and 23 are arranged on the first wiring layer 4 corresponds to and overlaps with the region (the trench capacitor area 51) where the trench capacitors 3 occupy on the first surface 2*a* of the semiconductor substrate 2.

An exemplary manner of arranging the connecting terminals evenly on the first wiring layer 4 is defined as bellow. As shown in FIG. 3(*a*), in this exemplary embodiment, the first connecting terminal 21 and the third connecting terminal 23 are evenly arranged on the first wiring layer 4, because the surface of the first wiring layer 4 is divided virtually and evenly in two by the virtual line X. The virtual points X1, X2 are the center points of the divided areas. The first connecting terminal 21 is arranged over the center point X1. The third connecting terminal 23 is arranged over the center point X2. In a similar manner, if there are three connecting terminals on the first wiring layer 4, the three connecting terminals may be arranged over the respective center points of three evenly divided areas of the first wiring layer 4. If there are four connecting terminals on the first wiring layer 4, the four connecting terminals may be arranged over the respective center points of four evenly divided areas of the first wiring layer 4.

Another exemplary manner of arranging the connecting terminals is defined by distances between the connecting terminals and the edge part of the wiring layer and between the TSVs and the semiconductor substrate 2. In this embodiment, the first connecting terminal 21 and the third connecting terminal 23 may be defined by two different distances— $1^{st}$ distance L1 and $2^{nd}$ distance and L2. As shown in FIG. 3(a), the 1st distance L1 is a distance between the connecting terminal 21 and the edge part of the first wiring layer 4, which may be in a range of 50 micrometer to 100 micrometer. As shown in FIG. 3 (b), the 2nd distance L2 is a distance between the TSV 11 and the edge part of the semiconductor substrate 2, which may be in a range of 10 micrometer to 20 micrometer. Similarly, as shown in FIG. 3(a), the 1st distance L1 is a minimum distance between the connecting terminal 23 and the edge part of the first wiring layer 4, which may be in a range of 50 micrometer to 100 micrometer. As shown in FIG. 3(b), the 2nd distance L2 is a minimum distance between the TSV 12 and the edge part of the semiconductor substrate 2, which may be in a range of 10 micrometer to 20 micrometer. The 1st distance and the 2nd distance are set such that the 1st distance is longer than the 2nd distance.

The second connecting terminal 22 and the fourth connecting terminal 24 may be also arranged dispersedly and evenly on the second wiring layer 5 in a same manner as the first connecting terminal 21 and the third connecting terminal 23, or may be in a different manner from the first and third connecting terminals 21 and 23.

As described above, the plurality of connecting terminals including the first connecting terminal 21 through the fourth connecting terminal 24 are arranged dispersively over the entire area of the first wiring layer 4 and the second wiring layer 5 of the semiconductor device 1. By this structural arrangement, when the semiconductor device 1 is connected to the other substrate or other cables, the stress induced by the connecting process is dispersed over the entire area of the first wiring layer 4 and the second wiring layer 5 of the semiconductor device 1. As a result, the damage typically caused by the stress concentration to the semiconductor device 1 by connecting process can be minimized, if not prevented.

On the other hand, the first TSV 11 and the second TSV 12 penetrate the semiconductor substrate 2 at the outer area of the trench capacitor area 51. As shown in FIG. 3(b), the first TSV 11 and the second TSV 12 are arranged at the surrounding areas 52, 53, respectively. By this structural arrangement, the trench capacitor area 51 occupies greater part of the first surface 2a, which may account for at least 75% or more is desirable of the entire area of the first surface 2a, thereby increasing the amount of electric charge of the semiconductor device 1.

Second Embodiment

Figure 4:
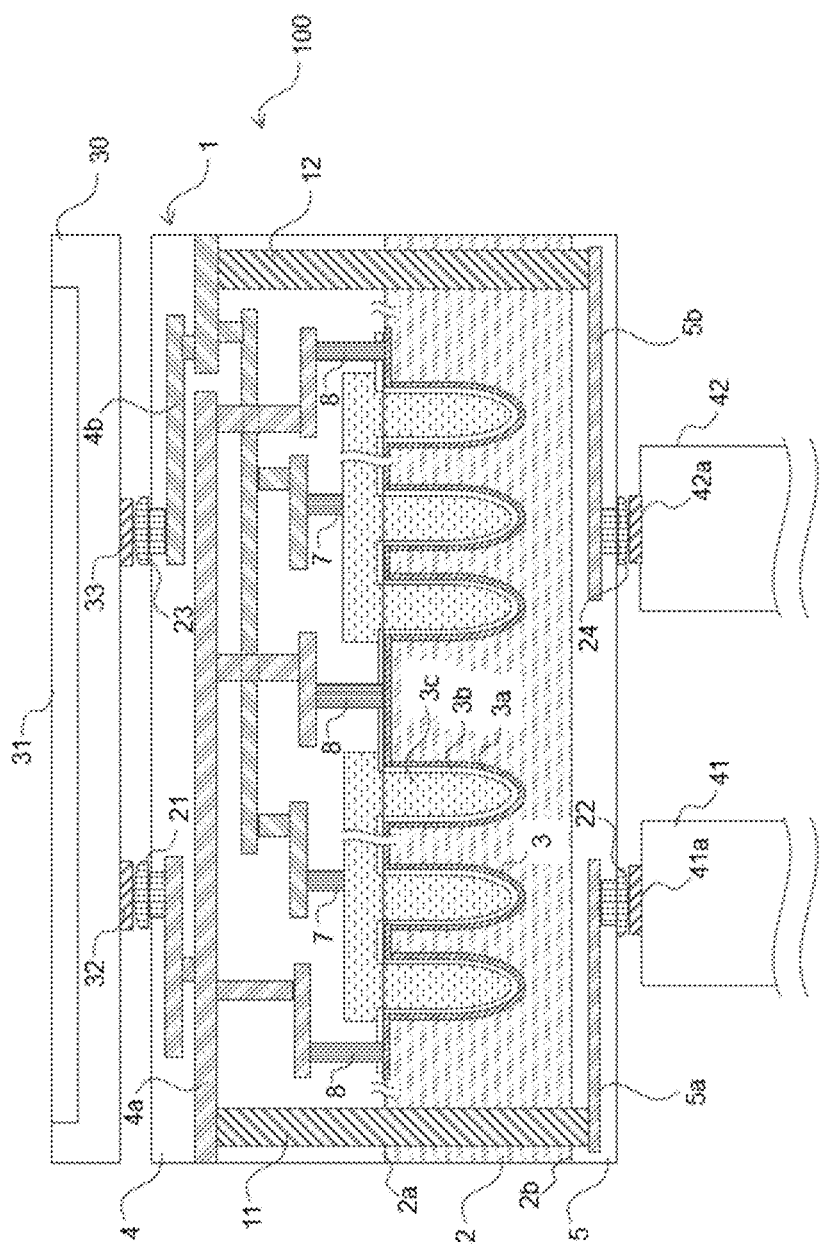
FIG. 4 is a cross section view schematically illustrating an image unit according to a second exemplary embodiment.

FIG. 4 is a cross section view of an image unit 100 according to the second embodiment. The image unit 100 may include the semiconductor device 1 and the image sensor 30. The image sensor 30 may be a square or rectangle plate shape, or a proper shape that matches with the semiconductor device 1. The image sensor 30 may have the vertical width and the horizontal width with a range of 500 micrometer to 1500 micrometer, which is the same as the semiconductor device 1. The image sensor 30 includes an image pixel 31 on a front surface of the image sensor 30. The image sensor 30 includes a VDD terminal 32 and a GND terminal 33 on a back surface of the image sensor 30.

When the image sensor 30 and the semiconductor device 1 are stacked together, the back surface of the image sensor 30 and the first surface 2a of the semiconductor substrate 2 may face each other. Thus, the VDD terminal 32 is connected to the first connecting terminal 21, and the GND terminal 33 is connected to the third connecting terminal 23 by a bump connecting process or the like.

The VDD cable 41 and the GND cable 42 may be arranged at one side of the second surface 2b of the semiconductor substrate 2. The VDD cable 41 transmits the VDD voltage, and the GND cable 42 transmits the GND voltage. The VDD cable 41 includes a tip terminal 41a that is connected to the second connecting terminal 22. The GND cable 42 includes a tip terminal 42a that is connected to the fourth connecting terminal 24.

The VDD voltage may be supplied to the VDD cable 41 from an outer voltage source (not shown). The GND voltage may be supplied to the GND cable 42 from the same outer voltage source or a different outer voltage source.

The VDD voltage passes through the VDD cable 41, the second connecting terminal 22, the wiring 5a of the second wiring layer 5, the first TSV 11, the wiring 4a of the first wiring layer 4 and the substrate contact 8. The substrate contact 8 supplies the VDD voltage to the first electrode 3a.

The GND voltage passes through the GND cable 42, the fourth connecting terminal 24, the wiring 5b of the second wiring layer 5, the second TSV 12, the wiring 4b of the first wiring layer 4 and the gate contact 7. The gate contact 7 supplies GND voltage to the second electrode 3c. By supplying the VDD voltage and the GND voltage to the substrate contact 8 and gate contact 7, respectively, the trench capacitors 3 accumulate the electric charge.

The VDD voltage also passes through the first TSV 11, the wiring 4a of the first wiring layer 4 and the first connecting terminal 21. The first connecting terminal 21 supplies the VDD voltage to the VDD terminal 32 of the image sensor 30. The GND voltage also passes through the second TSV 12, the wiring 4b of the first wiring layer 4 and the third connecting terminal 23. The third connecting terminal 23 supplies the GND voltage to the GND terminal 33 of the image sensor 30. The image sensor 30 drives the image pixel 31 by using the VDD voltage and the GND voltage, and generates an image signal stably.

The process of stabilizing the VDD voltage by the semiconductor device 1 is described as follows. The outer voltage source (not shown) may supply the VDD voltage to the VDD cable 41. A value of the VDD voltage supplied to the VDD cable 41 may be a predetermined value (a first value, such as 3.3V) at normal operation. The VDD voltage having the first value is supplied to the image sensor 30, and the image sensor 30 generates the image signal by using the VDD voltage having the first value. However, the value of VDD voltage may drop from the first value to a second value (such as 3.0V) due to a disturbance or the other factors. And the VDD voltage supplied to the image sensor 30 may drop as well. In this situation, the trench capacitors 3 of the semiconductor device 1 accumulate the electric charge according to the first value of VDD voltage before the voltage drops. And the trench capacitors 3 of the semiconductor device 1 increase the value of the VDD voltage supplied to the image sensor 30 by using the accumulated electric charge such that the value of the VDD voltage maintains the first value. As a result, the trench capacitors 3 stabilize the value of the VDD voltage supplied to the image sensor 30. The image sensor 30 is able to generate a stable image signal even if the value of the VDD voltage drops.

As another exemplary embodiment when the semiconductor device 1 and the image sensor 30 are stacked together, the back surface of the image sensor 30 and the second surface 2b of the semiconductor substrate 2 may face each other. In this case, the VDD terminal 32 is connected to the second connecting terminal 22, and the GND terminal 33 is connected to the fourth connecting terminal 24 (not shown).

Third Embodiment

Figure 5:
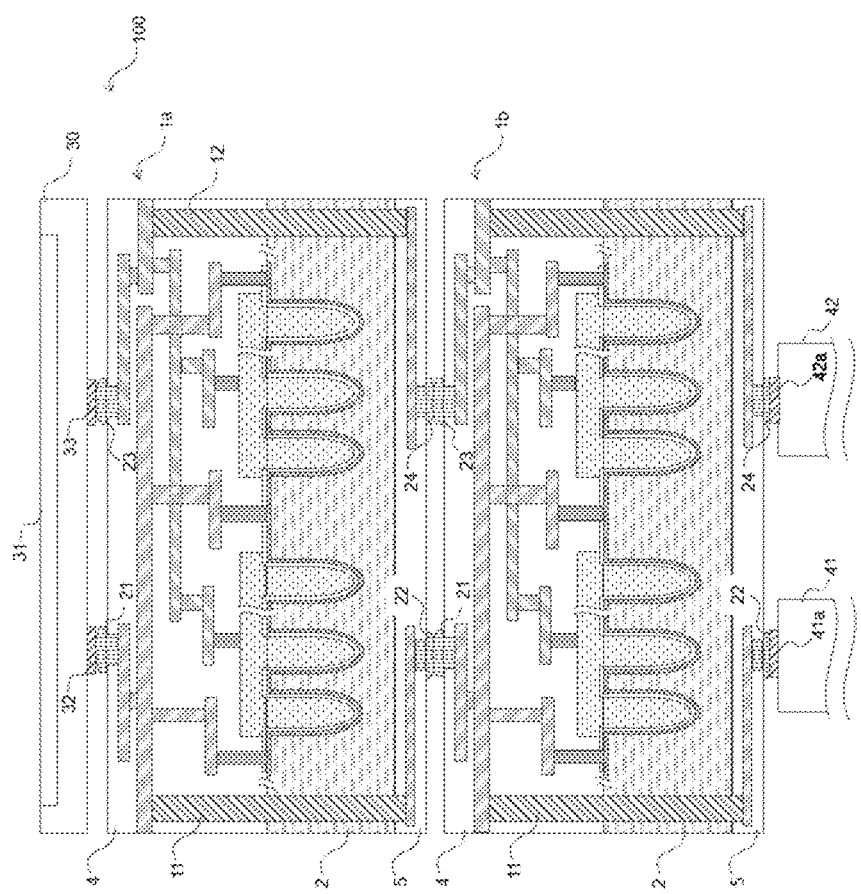
FIG. 5 is a cross section view schematically illustrating an image unit according to a third exemplary embodiment.

FIG. 5 is a cross section view schematically showing the image unit according to the third embodiment. As shown in FIG. 5, a semiconductor device 1a is stacked with an adjacent semiconductor device 1b. The exposed surface of the second wiring layer 5 of the semiconductor device 1a and the exposed surface of the first wiring layer 4 of the semiconductor device 1b face each other. In this situation, the second connecting terminal 22 and fourth connecting terminal 24 of the semiconductor device 1a are connected with the first connecting terminal 21 and third connecting terminal 23 of the adjacent semiconductor device 1b, respectively.

Also, the back surface of the image sensor 30 and the exposed surface of the first wiring layer 4 of the semiconductor device 1 face each other. The VDD terminal 32 is connected to the first connecting terminal 21. The GND terminal 33 is connected to the third connecting terminal 23.

The VDD cable 41 and the GND cable 42 are arranged at the side of the exposed surface of the second wiring layer 5 of the semiconductor device 1b. The tip terminal 41a of the VDD cable 41 is connected to the second connecting terminal 22. The tip terminal 42a of the GND cable 42 is connected to the fourth connecting terminal 24.

As another exemplary embodiment of stacking the semiconductor devices 1a and 1b, the exposed surface of the second wiring layer 5 of the semiconductor device 1a and the exposed surface of the second wiring layer 5 of the semiconductor device 1b may face each other (not shown). In this case, the second connecting terminal 22 and fourth connecting terminal 24 of the semiconductor device 1a are connected with the second connecting terminal 22 and fourth connecting terminal 24 of the adjacent semiconductor device 1b, respectively.

Also, as another exemplary embodiment of stacking semiconductor devices 1a and 1b, the exposed surface of the first wiring layer 4 of the semiconductor device 1a and the exposed surface of the first wiring layer 4 of the semiconductor device 1b may face each other (not shown). In this case, the first connecting terminal 21 and third connecting terminal 23 of the semiconductor device 1a are connected with the first connecting terminal 21 and third connecting terminal 23 of the adjacent semiconductor device 1b, respectively.

As described above, the semiconductor device 1a may be stacked with the adjacent semiconductor device 1b in various manners. The amount of electric charge with respect to the image sensor 30 is increased by stacking the plurality of the semiconductor devices. As a result, the VDD voltage supplied to the image sensor 30 is more stabilized, thereby generating stable image signals from the image sensor 30.

Fourth Embodiment

Figure 6:
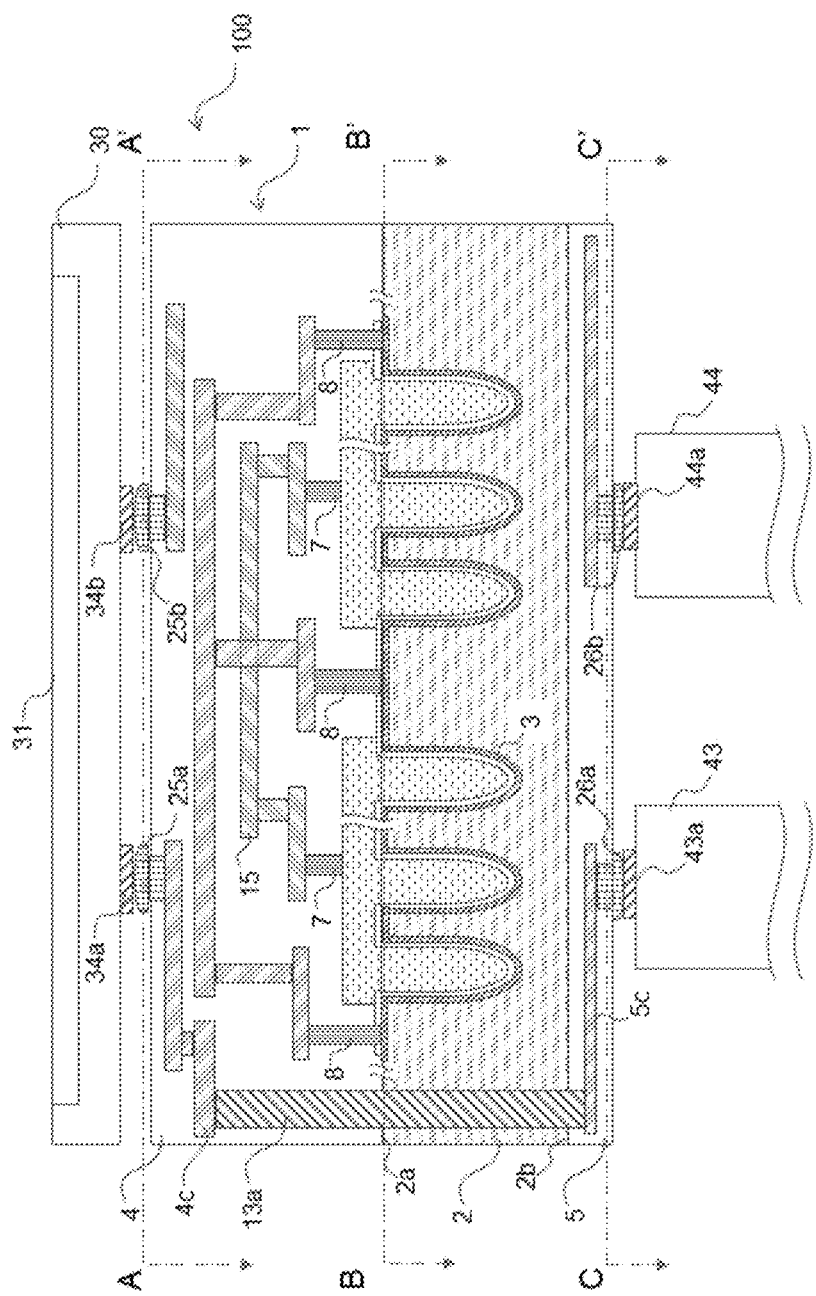
FIG. 6 is a cross section view schematically illustrating a semiconductor device according to a fourth exemplary embodiment.

FIG. 6 is a cross section view of the semiconductor device 1 according to the fourth embodiment. FIGS. 7(a)-7(c) are perspective views of certain components of the semiconductor device 1. FIGS. 8(a)-8(c) are plain views of these components of the semiconductor device 1.

Figure 7:
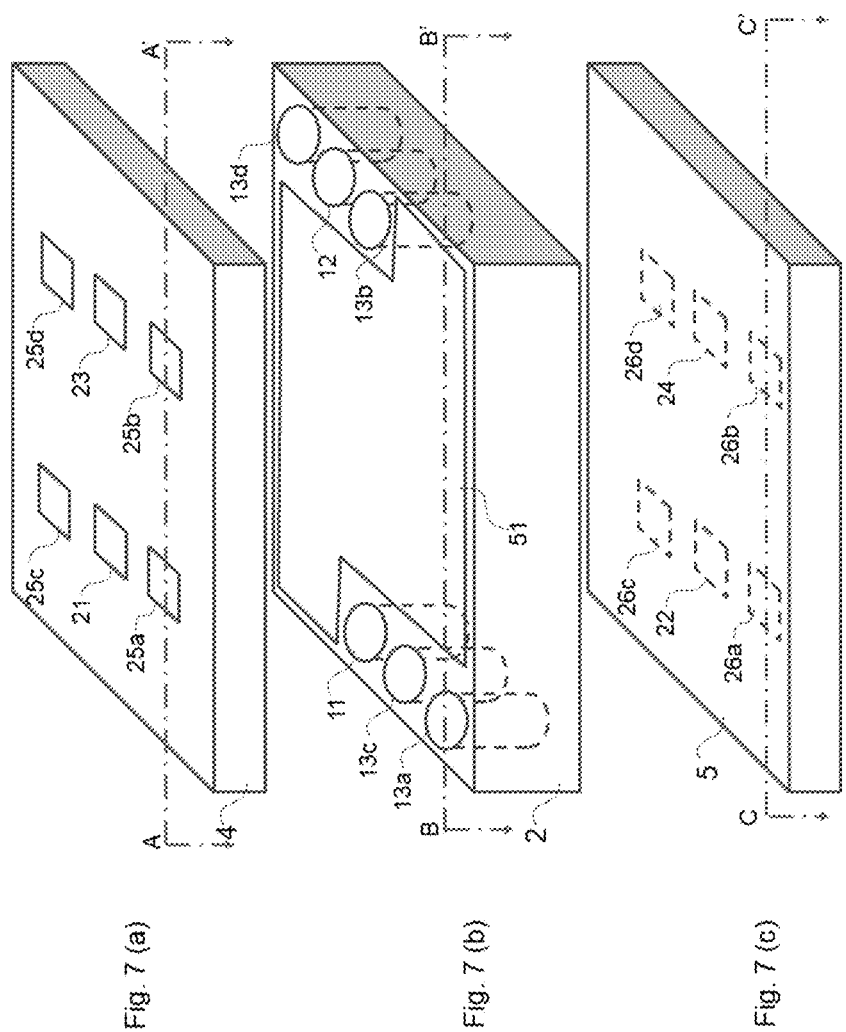
FIGS. 7(a) to 7(c) are perspective views schematically illustrating certain components of the semiconductor device of FIG. 6.
Figure 8:
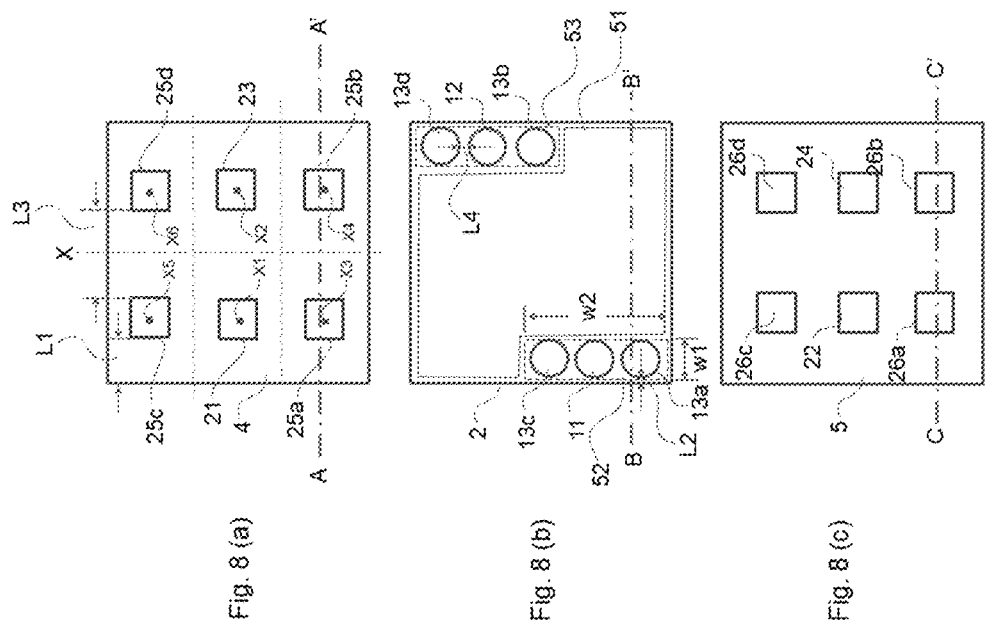
FIGS. 8(a) to 8(c) are plain views schematically illustrating the components of the semiconductor device of FIGS. 7(a) to 7(c), respectively.

FIG. 8 (a) indicates a plain view with respect to the arrows A-A' of FIG. 6 and FIG. 7 (a). FIG. 8 (b) indicates a plain view with respect to the arrows B-B' of FIG. 6 and FIG. 7 (b). FIG. 8 (c) indicates a plain view with respect to the arrows C-C' of FIG. 6 and FIG. 7 (c).

As shown in FIGS. 7(a)-7(c) and FIGS. 8(a)-(c), the semiconductor substrate 2 may further include third TSVs 13a, 13b, 13c and 13d. The first wiring layer 4 may further include fifth connecting terminals 25a, 25b, 25c and 25d. The second wiring layer 5 may further include sixth connecting terminals 26a, 26b, 26c and 26d.

The third TSVs 13a, 13b, 13c and 13d may transmit image signal, clock signal, synchro signal and second VDD voltage. The image signal generated by the image sensor 30 may be transmitted to a processor unit (not shown) via the third TSV 13a. The processor unit may send the clock signal to the image sensor 30 via the third TSV 13b. The clock signal is used at the image sensor 30 for controlling the timing of generating the image signal. The processor unit sends the synchro signal to the image sensor 30 via the third TSV 13c. The synchro signal is used at the image sensor 30 for synchronizing the image signal and the processor unit. The outer voltage source supplies the second VDD voltage to the image sensor 30 via the third TSV 13d. The second VDD voltage may be used at the image sensor 30.

As shown in FIG. 6, the third TSV 13a and the fifth connecting terminal 25a are connected by the wiring 4c in the first wiring layer 4. The third TSV 13a and the sixth connecting terminal 26a are connected by the wiring 5c in the second wiring layer 5. In the same manner as the third TSV 13a, the third TSVs 13b, 13c and 13d are connected to the fifth connecting terminals 25b, 25c and 25d by the wiring 4c in the first wiring layer 4, respectively. (FIG. 7(a)). The third TSVs 13b, 13c and 13d are connected to the sixth connecting terminals 26b, 26c and 26d by the wiring 5c in the second wiring layer 5, respectively. (FIG. 9(c)).

The image sensor 30 includes an image signal terminal 34a and a clock signal terminal 34b. The image sensor 30 may further includes a synchro signal terminal 34c and a second VDD terminal 34d (not shown).

In the case that the back surface of the image sensor 30 and the first surface 2a of the semiconductor substrate 2 face each other, the image signal terminal 34a is connected to the fifth connecting terminal 25a, and the clock signal terminal 34b is connected to the fifth connecting terminal 25b. The synchro signal terminal 34c and the second VDD terminal 34d are connected to the fifth connecting terminal 25c and 25d, respectively (not shown).

As shown in FIG. 8(b), the first TSV 11, the second TSV 12, the third TSVs 13a, 13b, 13c and 13d may be arranged at an area outside (the outer area of) the trench capacitor area 51. The outer area of the trench capacitor area 51 may include the surrounding areas 52, 53 that surround or sandwich the trench capacitor area 51, which is an area on the semiconductor substrate 2 occupied by the trench capacitors 3. As an example, the surrounding areas 52, 53 may be arranged at the diagonal edge part of the semiconductor substrate 2, respectively. The surrounding areas 52, 53 may be rectangle shape or may be a different shape that is suitable for arranging the TSVs and for allowing the trench capacitor area 51 to have a maximized size. The surrounding areas 52, 53 may have the horizontal width (W1) in a range of 10 micrometer to 50 micrometer, and the vertical width (W2) in a range of 50 micrometer to 200 micrometer. The first TSV 11, the third TSVs 13a and 13c may be arranged at the surrounding area 52. The second TSV 12, the third TSVs 13b and 13d may be arranged at the surrounding area 53.

As shown in FIGS. 8(a) and 8(c), the plurality of connecting terminals including the first connecting terminal 21 through the sixth connecting terminal 26a, 26b, 26c and 26d may be arranged dispersively over the entire area of the first wiring layer 4 and the second wiring layer 5 of the semiconductor device 1. These connecting terminals may be arranged in various patterns that are suitable for the arrangement except that these connecting terminals do not overlap with the TSVs from a top view of the semiconductor device 1.

As shown in FIG. 8(a), the first connecting terminal 21, the third connecting terminal 23, and the fifth connecting terminals 25a, 25b, 25c and 25d are "arranged dispersively" on the first wiring layer 4. An exemplary manner of arranging the first connecting terminal 21, the third connecting terminal 23, and the fifth connecting terminals 25a, 25b, 25c and 25d on the first wiring layer 4 (the meaning of "arranged dispersively") is described as follows.

For example, the first connecting terminal 21, the third connecting terminal 23, and the fifth connecting terminals 25a, 25b, 25c and 25d may be evenly spaced apart on a region of the first wiring layer 4. The region where the first connecting terminal 21, the third connecting terminal 23, the fifth connecting terminals 25a, 25b, 25c and 25d are arranged on the first wiring layer 4 corresponds to and overlaps with the region of the first surface 2a that the trench capacitors 3 occupy on the semiconductor substrate 2 (the trench capacitor area 51).

Another exemplary manner of arranging the first connecting terminal 21, the third connecting terminal 23, and the fifth connecting terminals 25a, 25b, 25c and 25d evenly on the first wiring layer 4 is defined as bellow. As shown in FIG. 8(a), the surface of the first wiring layer 4 may be divided virtually and evenly in six areas by the virtual line X. The virtual points X1, X2, X3, X4, X5 and X6 are the respective center points of the divided six (6) areas. The third connecting terminal 23, and the fifth connecting terminals 25a, 25b, 25c and 25d may be arranged over the center points X1, X2, X3, X4, X5 and X6, respectively.

Still another exemplary manner of arranging the first connecting terminal 21, the third connecting terminal 23, and the fifth connecting terminals 25a, 25b, 25c and 25d is defined by distances between the connecting terminals and the edge part of the first wiring layer 4 and between the TSVs and the edge part of the semiconductor substrate 2. For example, a 1st distance L1 may be a distance between the connecting terminals and the edge part of the first wiring layer 4 in a range of 50 micrometer to 100 micrometer. The 2nd distance L2 may be a distance between the TSVs 11, 12 and 13a-13d and the edge part of the semiconductor substrate 2 in a range of 10 micrometer to 20 micrometer. The 1st distance and the 2nd distance are set such that the 1st distance is longer than the 2nd distance.

Still another exemplary manner of arranging the first connecting terminal 21, the third connecting terminal 23, and the fifth connecting terminals 25a, 25b, 25c and 25d may be defined by distances between adjacent connecting terminals and between adjacent TSVs. For example, a 3rd distance L3 may be a distance between the adjacent connecting terminals in a range of 50 micrometer to 80 micrometer. A 4th distance L4 may be a distance between the adjacent TSVs in a range of 10 micrometer to 20 micrometer. The 3rd distance and the 4th distance are set such that the 3rd distance is longer than the 4th distance.

The second connecting terminal 22, the fourth connecting terminal 24, and the sixth connecting terminals 26a, 26b, 26c and 26d may be also arranged dispersedly and evenly on the second wiring layer 5 as the same manner of arranging the first connecting terminal 21, the third connecting terminal 23, and the fifth connecting terminals 25a, 25b, 25c and 25d.

As described above, the plurality of connecting terminals including the first connecting terminal 21 through sixth connecting terminal 26a, 26b, 26c and 26d may be arranged dispersively over the entire area of the first wiring layer 4 and the second wiring layer 5 of the semiconductor device 1. By such a structural configuration, when the semiconductor device 1 is connected to the other substrate or other cables, the stress induced by a connecting process is dispersed over the entire area of the first wiring layer 4 and the second wiring layer 5 of the semiconductor device 1. As a result, the damage caused by the stress concentration to the semiconductor device 1 by connecting process can be minimized or mitigated.

Referring to FIG. 8(b), the first TSV 11, the second TSV 12, and the third TSVs 13a, 13b, 13c and 13d penetrate the semiconductor substrate 2 at the outer area of the trench capacitor area 51. The first TSV 11, the second TSV 12, and the third TSVs 13a, 13b, 13c and 13d may be arranged at the surrounding areas 52, 53. According to this exemplary structural arrangement, the trench capacitor area 51 occupies the greater part of the first surface 2a, which may be up to at least 70% of the entire area of the first surface 2a, thereby increasing the amount of electric charge of the semiconductor device 1. Further, the third TSVs 13a, 13b, 13c and 13d may be utilized to translate the image signal, the clock signal, the synchro signal, the second VDD voltage in the thickness direction of the semiconductor device 1, respectively.

Fifth Embodiment

Figure 9:
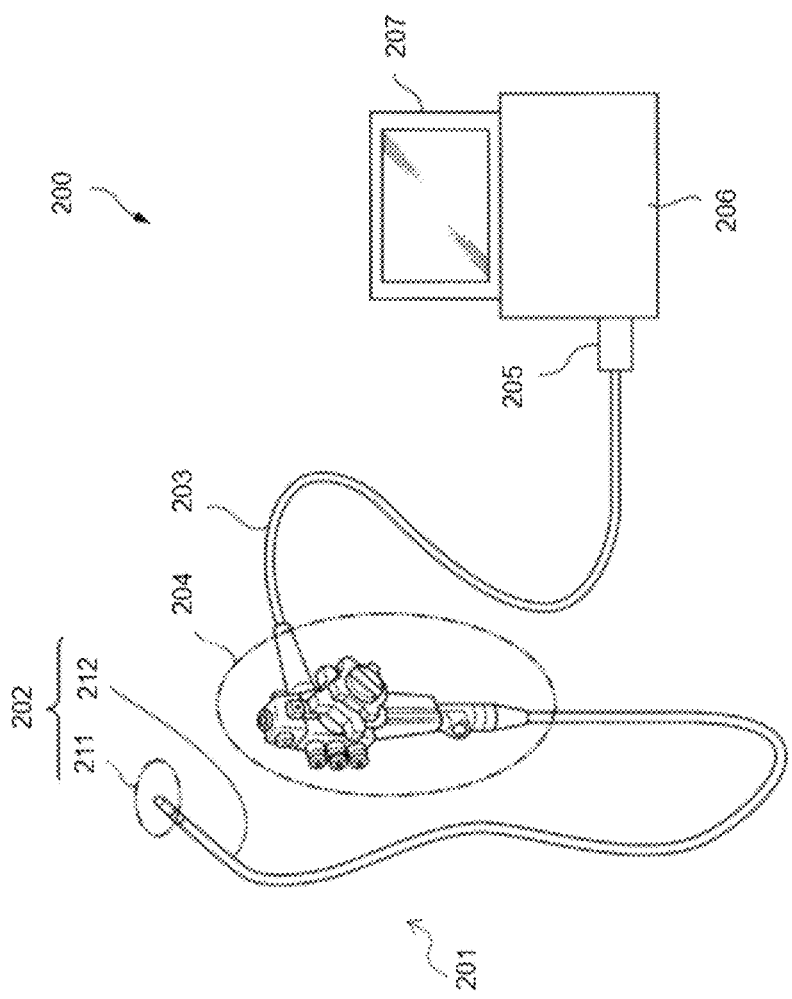
FIG. 9 is a perspective view schematically illustrating an endoscope system according to a fifth exemplary embodiment.

FIG. 9 is a perspective view of an endoscope system 200 according to the fifth embodiment. As shown in FIG. 9, the endoscope system 200 includes an endoscope 201, a processor 206, and a display device 207. The endoscope 201 includes a transmission cable 203, a manipulation unit 204, a connector unit 205 and an insertion portion 202.

The insertion portion 202 is a part of the transmission cable 203. The insertion portion 202 is inserted into an object to be inspected. The insertion portion 202 includes a flexible bending portion 212 and a distal end portion 211. The flexible bending portion 212 may make bending motions in desirable directions by operating the manipulation unit 204.

Figure 10:
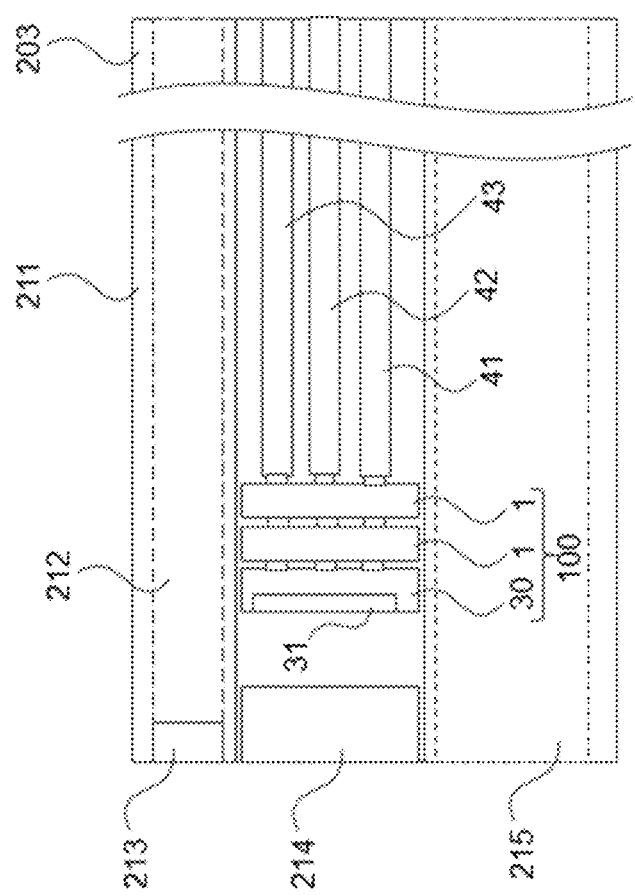
FIG. 10 is a cross section view schematically illustrating a distal end portion of the endoscope system of FIG. 9.

Any of the disclosed image units 100 according to the above embodiments may be arranged at the distal end portion 211. FIG. 10 is a cross section view of the distal end portion 211 of the endoscope 201. The distal end portion 211 includes a light guide 212, an illumination lens 213, an image lens 214, a treatment tool passage 215, and the image unit 100. The light guide 212 transmits illumination light from the light source device (not shown). The illumination lens 213 irradiate the object (not shown) with the illumination light. The treatment tool (not shown) is inserted in the treatment tool passage 215.

The image unit 100 may be arranged in the distal end portion 211. The front surface having the image pixel 31 of the image sensor 30 faces the image lens 214. The image lens 214 forms an image of the object on the image pixel 31 of the image sensor 30.

The VDD cable 41, the GND cable 42 and the image signal cable 43 may be arranged in the transmission cable 203. The VDD cable 41, the GND cable 42 and the image signal cable 43 each have one end portion connected to the semiconductor device 1 of the image unit 100. The VDD cable 41, the GND cable 42 and the image signal cable 43 each have the other end portion connected to the connector unit 205.

The clock signal cable, the synchro signal cable and the second VDD cable may be arranged inside the transmission cable 203 (not shown). The clock signal cable, the synchro signal cable and the second VDD cable each have one end portion connected to the semiconductor device 1 of the image unit 100. The clock signal cable, the synchro signal cable and the second VDD cable each have the other end portion connected to the connector unit 205.

The image unit 100 of the endoscope 201 generates an image signal (image data) by capturing an internal image of the object. The image unit 100 outputs the generated image signal to the image signal cable 43 in the transmission cable 203. The processor 206 receives the image signal from the image signal cable 43.

The connector unit 205 connects the endoscope 201 and the processor 206. The connector unit 205 performs a predetermined signal processing of the image signal output from the image unit 100. The connector unit 205 also performs A/D convert that an analog image signal is converted into a digital image signal. The connector unit 205 outputs the digital image signal to the processor 206.

The processor 206 performs the predetermined image processing of the image signal output from the connector unit 205. The processor 206 also controls the endoscope system 200. The processor 206 may include a voltage source. The voltage source may supply VDD voltage and VDD voltage to the VDD cable 41 and the GND cable 42, respectively.

The display device 207 displays an image corresponding to the image signal processed by the processor 206. The display device 207 may also display various types of information of the endoscope system 200. The endoscope system 200 includes a light source device (not shown) for generating illumination light with which the object is irradiated.

As described above, the image unit 100 may be arranged in the distal end portion 211. The semiconductor device 1 of the image unit 100 stabilizes the VDD voltage supplied to the image sensor 30. As a result, the image sensor 30 generates stable image signals. Also, the semiconductor device 1 and the image sensor 30 may be stacked in a longitudinal direction of the distal end portion 211. By such a structural arrangement, the semiconductor device 1 does not make the diameter of the image unit 100 larger, thereby ensuring a smaller diameter of the endoscope 201.

It will be apparent to those skilled in the art that various modifications and variations can be made in the semiconductor device, image unit and endoscope system using the semiconductor device of the present invention without departing from the spirit or scope of the invention. Thus, it is intended that the present invention cover the modifications and variations of this invention provided they come within the scope of the appended claims and their equivalents.

What is claimed is:

1. A semiconductor device, comprising:
   a semiconductor substrate having a first surface and a second surface opposing to each other;
   a trench capacitor arranged on the first surface of the semiconductor substrate;
   a first wiring layer arranged on the first surface of the semiconductor substrate and covering the trench capacitor;
   a second wiring layer arranged on the second surface of the semiconductor substrate;
   a first TSV (through-silicon via) penetrating the semiconductor substrate outside the trench capacitor;
   a second TSV (through-silicon via) penetrating the semiconductor substrate outside the trench capacitor;
   a first connecting terminal arranged on the first wiring layer, and connected to the first TSV;
   a second connecting terminal arranged on the second wiring layer, and connected to the first TSV;
   a third connecting terminal arranged on the first wiring layer, and connected to the second TSV; and
   a fourth connecting terminal arranged on the second wiring layer, and connected to the second TSV,
   wherein a plurality of connecting terminals including the first through fourth connecting terminals are arranged dispersively over an entire area of the first wiring layer and the second wiring layer of the semiconductor device,
   wherein the first surface of the semiconductor substrate includes a first region where the trench capacitor occupies and a second region where the first and second TSVs pass through, and
   wherein the plurality of connecting terminals including at least the first and third connecting terminals are evenly spaced apart on a region of the first wiring layer, the region of the first wiring layer overlapping with the first region of the first surface of the semiconductor substrate where the trench capacitor occupies.

2. The semiconductor device according to claim 1, wherein the first region of the first surface account is larger than the second region of the first surface of the semiconductor substrate.

3. A semiconductor device, comprising:
   a semiconductor substrate having a first surface and a second surface opposing to each other;
   a trench capacitor arranged on the first surface of the semiconductor substrate;
   a first wiring layer arranged on the first surface of the semiconductor substrate and covering the trench capacitor;
   a second wiring layer arranged on the second surface of the semiconductor substrate;
   a first TSV (through-silicon via) penetrating the semiconductor substrate outside the trench capacitor;
   a second TSV (through-silicon via) penetrating the semiconductor substrate outside the trench capacitor;
   a first connecting terminal arranged on the first wiring layer, and connected to the first TSV;
   a second connecting terminal arranged on the second wiring layer, and connected to the first TSV;
   a third connecting terminal arranged on the first wiring layer, and connected to the second TSV; and
   a fourth connecting terminal arranged on the second wiring layer, and connected to the second TSV,
   wherein a plurality of connecting terminals including the first through fourth connecting terminals are arranged dispersively over an entire area of the first wiring layer and the second wiring layer of the semiconductor device, and
   wherein the first wiring layer includes a substrate contact and a gate contact.

4. The semiconductor device according to claim 3, wherein the trench capacitor includes a first electrode, a second electrode and a dielectric layer, the first electrode and the second electrode sandwich the dielectric layer, and the gate contact is connected the first electrode, and the substrate contact is connected to the second electrode.

5. The semiconductor device according to claim 3, wherein the substrate contact is connected to the second TSV, and the gate contact is connected to the first TSV by a wiring of the first wiring layer.

6. The semiconductor device according to claim 3, wherein the semiconductor device is stacked with an adjacent semiconductor device, such that the first and third connecting terminals of the semiconductor device are connected with second and fourth connecting terminals of the adjacent semiconductor device, respectively.

7. The semiconductor device according to claim 3, wherein the semiconductor device is stacked with an adjacent semiconductor device, such that the first and third connecting terminals of the semiconductor device are connected with first and third connecting terminals of the adjacent semiconductor device, respectively.

8. A semiconductor device, comprising:
a semiconductor substrate having a first surface and a second surface opposing to each other;
a trench capacitor arranged on the first surface of the semiconductor substrate;
a first wiring layer arranged on the first surface of the semiconductor substrate and covering the trench capacitor;
a second wiring layer arranged on the second surface of the semiconductor substrate;
a first TSV (through-silicon via) penetrating the semiconductor substrate outside the trench capacitor;
a second TSV (through-silicon via) penetrating the semiconductor substrate outside the trench capacitor;
a first connecting terminal arranged on the first wiring layer, and connected to the first TSV;
a second connecting terminal arranged on the second wiring layer, and connected to the first TSV;
a third connecting terminal arranged on the first wiring layer, and connected to the second TSV; and
a fourth connecting terminal arranged on the second wiring layer, and connected to the second TSV,
wherein a plurality of connecting terminals including the first through fourth connecting terminals are arranged dispersively over an entire area of the first wiring layer and the second wiring layer of the semiconductor device,
wherein the first surface of the semiconductor substrate includes a first region where the trench capacitor occupies and a second region where the first and second TSVs pass through, and
wherein the plurality of connecting terminals including at least the second and fourth connecting terminals are evenly spaced apart on a region of the second wiring layer, the region of the second wiring layer corresponding to the first region of the first surface of the semiconductor substrate where the trench capacitor occupies.

9. The semiconductor device according to claim 8, wherein the first region of the first surface account is larger than the second region of the first surface of the semiconductor substrate.

10. A semiconductor device, comprising:
a semiconductor substrate having a first surface and a second surface opposing to each other;
a trench capacitor arranged on the first surface of the semiconductor substrate;
a first wiring layer arranged on the first surface of the semiconductor substrate and covering the trench capacitor;
a second wiring layer arranged on the second surface of the semiconductor substrate;
a first TSV (through-silicon via) penetrating the semiconductor substrate outside the trench capacitor;
a second TSV (through-silicon via) penetrating the semiconductor substrate outside the trench capacitor;
a first connecting terminal arranged on the first wiring layer, and connected to the first TSV;
a second connecting terminal arranged on the second wiring layer, and connected to the first TSV;
a third connecting terminal arranged on the first wiring layer, and connected to the second TSV; and
a fourth connecting terminal arranged on the second wiring layer, and connected to the second TSV,
wherein a plurality of connecting terminals including the first through fourth connecting terminals are arranged dispersively over an entire area of the first wiring layer and the second wiring layer of the semiconductor device, and
wherein the semiconductor device is stacked with an adjacent semiconductor device, such that the second and fourth connecting terminals of the semiconductor device are connected with second and fourth connecting terminals of the adjacent semiconductor device, respectively.

11. A semiconductor device, comprising:
a semiconductor substrate having a first surface and a second surface opposing to each other;
a trench capacitor arranged on the first surface of the semiconductor substrate;
a first wiring layer arranged on the first surface of the semiconductor substrate and covering the trench capacitor;
a second wiring layer arranged on the second surface of the semiconductor substrate;
a first TSV (through-silicon via) penetrating the semiconductor substrate outside the trench capacitor;
a second TSV (through-silicon via) penetrating the semiconductor substrate outside the trench capacitor;
a first connecting terminal arranged on the first wiring layer, and connected to the first TSV;
a second connecting terminal arranged on the second wiring layer, and connected to the first TSV;
a third connecting terminal arranged on the first wiring layer, and connected to the second TSV; and
a fourth connecting terminal arranged on the second wiring layer, and connected to the second TSV,
wherein a plurality of connecting terminals including the first through fourth connecting terminals are arranged dispersively over an entire area of the first wiring layer and the second wiring layer of the semiconductor device, and
wherein the plurality of the connecting terminals do not overlap with the TSVs from a top view of the semiconductor device.

12. An image unit, comprising:
an image sensor including an image pixel on a front surface, and a ground terminal and a VDD terminal on a back surface; and
a semiconductor device,
wherein the semiconductor device includes:
a semiconductor substrate having a first surface and a second surface opposing to each other;

a trench capacitor arranged on the first surface of the semiconductor substrate;
a first wiring layer arranged on the first surface of the semiconductor substrate and covering the trench capacitor;
a second wiring layer arranged on the second surface of the semiconductor substrate;
a first TSV (through-silicon via) penetrating the semiconductor substrate outside the trench capacitor;
a second TSV (through-silicon via) penetrating the semiconductor substrate outside the trench capacitor;
a first connecting terminal arranged on the first wiring layer, and connected to the first TSV;
a second connecting terminal arranged on the second wiring layer, and connected to the first TSV;
a third connecting terminal arranged on the first wiring layer, and connected to the second TSV; and
a fourth connecting terminal arranged on the second wiring layer, and connected to the second TSV,
wherein a plurality of connecting terminals including the first through fourth connecting terminals are arranged dispersively over an entire area of the first wiring layer and the second wiring layer of the semiconductor device, and
wherein the first and third connecting terminals of the semiconductor device are connected with the VDD and the ground terminals of the image sensor, respectively.

13. An endoscope, comprising:
an image unit according to claim 12.

14. An image unit, comprising:
an image sensor including an image pixel on a front surface and a ground terminal and a VDD terminal on a back surface; and
a semiconductor device,
wherein the semiconductor device includes:
a semiconductor substrate having a first surface and a second surface opposing to each other;
a trench capacitor arranged on the first surface of the semiconductor substrate;
a first wiring layer arranged on the first surface of the semiconductor substrate and covering the trench capacitor;
a second wiring layer arranged on the second surface of the semiconductor substrate;
a first TSV (through-silicon via) penetrating the semiconductor substrate outside the trench capacitor;
a second TSV (through-silicon via) penetrating the semiconductor substrate outside the trench capacitor;
a first connecting terminal arranged on the first wiring layer, and connected to the first TSV;
a second connecting terminal arranged on the second wiring layer, and connected to the first TSV;
a third connecting terminal arranged on the first wiring layer, and connected to the second TSV; and
a fourth connecting terminal arranged on the second wiring layer, and connected to the second TSV,
wherein a plurality of connecting terminals including the first through fourth connecting terminals are arranged dispersively over an entire area of the first wiring layer and the second wiring layer of the semiconductor device, and
wherein the second and fourth connecting terminals of the semiconductor device are connected with the VDD and the ground terminals of the image sensor, respectively.

15. The image unit according to claim 14, wherein the plurality of connecting terminals includes at least a fifth connecting terminal on the first wire layer and a sixth connecting terminal on the second wire layer, and
wherein the fifth connecting terminal is connected to the sixth connecting terminal via a third TSV.

16. The image unit according to claim 14, wherein the third TSV translate at least one of image signal, clock signal and synchro signal.

17. An endoscope, comprising:
an image unit according to claim 14.

* * * * *